United States Patent [19]

Fodor et al.

[11] Patent Number: 5,021,597

[45] Date of Patent: Jun. 4, 1991

[54] NOVEL ACRYLIC ACID SALTS, A PROCESS FOR THEIR PREPARATION, PHARMACEUTICAL COMPOSITIONS CONTAINING THEM AND THEIR USE IN THE MEDICINE

[75] Inventors: Tamas Fodor; Janos Fischer; Laszlo Dobay; Ferenc Trischler; Elemer Ezer; Judit Matuz; Katalin Saghy; Laszlo Szporny; György Hajos, all of Budapest, Hungary

[73] Assignee: Richter Gedeon Vegyeszeti Gyar Rt., Budapest, Hungary

[21] Appl. No.: 551,519

[22] Filed: Jul. 11, 1990

[30] Foreign Application Priority Data

Jul. 14, 1989 [HU] Hungary ............................ 3570/89

[51] Int. Cl.$^5$ ............................ C07F 9/94; C07F 3/06
[52] U.S. Cl. ........................ 556/69; 556/64; 556/119; 514/925; 514/927
[58] Field of Search ............... 556/69, 64, 118, 119; 514/492, 494, 925, 927, 2

[56] References Cited

U.S. PATENT DOCUMENTS

| | | | |
|---|---|---|---|
| 636,216 | 10/1899 | Schaefer | 556/69 |
| 3,504,005 | 3/1970 | Moedritzer et al. | 556/64 X |
| 4,404,408 | 9/1983 | Wirth et al. | 556/64 X |
| 4,801,608 | 1/1989 | Bos et al. | 514/925 X |
| 4,866,039 | 9/1989 | Wootton et al. | 514/925 X |
| 4,940,695 | 7/1990 | Coveney et al. | 514/925 X |

*Primary Examiner*—Arthur C. Prescott
*Attorney, Agent, or Firm*—Herbert Dubno; Jonathan Myers

[57] ABSTRACT

Novel acrylic acid salts of formula

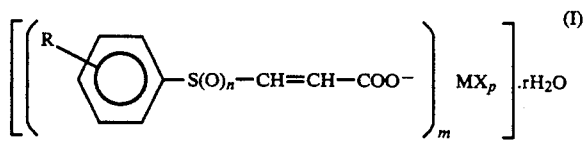

wherein
R represents a hydrogen or a halogen atom, a $C_{1-4}$alkyl, a $C_{1-4}$alkoxy or a nitro group,
M represents a cation derived from bismuth, zinc or a pharmaceutically acceptable organic base,
X represents an inorganic anion,
n is an integer of from 0 to 2,
m is an integer of from 1 to 3,
p is 0 or 1, and
r is an integer of from 0 to 6 having cytoprotective and antiulcer activities are provided. A process is also described for the preparation of said compounds.

14 Claims, No Drawings

NOVEL ACRYLIC ACID SALTS, A PROCESS FOR THEIR PREPARATION, PHARMACEUTICAL COMPOSITIONS CONTAINING THEM AND THEIR USE IN THE MEDICINE

The present invention is concerned with novel acrylic acid salts, a process for the preparation thereof, pharmaceutical compositions containing the same and their use in the medicine, particularly in the prophylaxis and treatment of ulcerations in mammals inclusive of man.

According to a first aspect of the present invention, there is provided a novel acrylic acid salt of formula

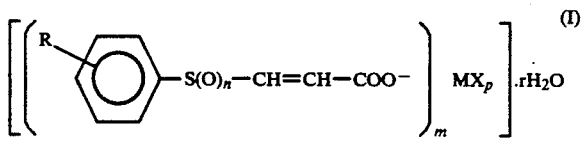

wherein

R represents a hydrogen or a halogen atom, a $C_{1-4}$alkyl, a $C_{1-4}$alkoxy or a nitro group, M represents a cation derived from bismuth, zinc or a pharmaceutically acceptable organic base, X represents an inorganic anion, n is an integer of from 0 to 2, m is an integer of from 1 to 3, p is 0 or 1, and r is an integer of from 0 to 6.

As for the structurally closest known compounds, reference is made ot the compounds of formula

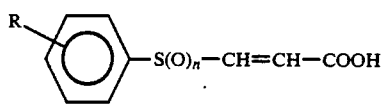

used as starting material for the preparation of the compounds of the present invention, and to their sodium salts, the preparation and non-pharmaceutical use of which have been described in a number of papers and patent specifications.

Those compounds of formula (II), wherein n is zero, and analogous compounds being different only in the meaning of R are referred to hereinafter as phenylthiopropenoic acid derivatives.

Those compounds of formula (II) wherein n is 1, and analogous compounds being different only in the meaning of R are referred to hereinafter as phenylsulfinylpropenoic acid derivatives.

Those compounds of formula (II), wherein n is 2, and analogous compounds being different only in the meaning of R are referred to hereinafter as phenylsulfonylpropenoic acid derivatives.

U.S. patent specification 2,532,291 describes the preparation of phenylthiopropenoic acid derivatives. No teaching is disclosed, however, concerning their use.

Japanese laid-open patent specifications 52-7919 and 52-7920 disclose the preparation of phenylthio-, phenylsulfinyl- and phenylsulfonylpropenoic acid derivatives and their alkaline metal salts. The compounds prepared in JP 52-7919 are declared as surface active agents.

Japanese laid-open patent specification 151,121 discloses the preparation of phenylthiopropenoic acid derivatives and their alkaline metal salts. These compounds are stated to be surface active agents and antibacterial agents and are suggested to be used as detergents, bactericidal or disinfecting agents, furthermore as cream bases.

Japanese laid-open patent specification 151,123 describes the preparation of phenylsulfinyl- and phenylsulfonylpropenoic acid derivatives. Alkali metal and alkaline earth metal salts of these compounds are also claimed but are not prepared. The use of these compounds as antibacterial agents, disinfecting agents, antifungal agents against mould as well as antioxidants is suggested.

European patent specification No. 40359 describes certain phenylsulfinylpropenoic acid derivatives useful as intermediates in the preparation of dyestuffs.

Surprisingly we have found, that the compounds of formula (I) and their salts can also be used as human medicaments in particular for the pre- and after-treatment of patients having or prone to have ulceration.

A steadily increasing part of the population is involved in the ulceration of the digestive tract. Ulcer induces a very strong pain in its active stage and bleeding can also occur. According to the traditional medication, the primary object is to reduce the pain, then to promote the healing of the injured tissues. Traditional medicaments (e.g. Pyrenzepine, Cimetidine, Omeprazole, etc.) have been intended to achieve the above effects by the reduction of the gastric acid level and inhibition of the secretion gastric acid, respectively. In the case of proper medication and diet, an ulcer is generally healed after 4 to 6 weeks. However, it happens frequently that the ulcer relapses and the medication should be recommenced.

Recent investigations are focussed increasingly to the so-called cytoprotective compounds. These compounds increase the protective ability of the stomach; thereby upon the administration of such compounds the probability of a relapse of an ulcer is significantly reduced or the emergence of ulcer can be prevented in a subject susceptible to ulcers.

Compounds exerting inhibitory activity on gastric acid secretion in addition to their cytoprotective activity are, of course, of particular interest.

Among the compounds of the present invention, there are several compounds having both cytoprotective and gastric acid secretion inhibitory activities. We have found, additionally, that the compounds of the invention exert prolonged action for both activities.

In the Tables below illustrating the results of biological investigations the following abbreviations are used:

A: bismuth tris [3-phenylsulfonyl-2(E)-propenoate] pentahydrate

B: zinc bis [phenylthio-2(Z)-propenoate] hydrate

C: monoethanolamine salt of 3-phenylsulfonyl-2(E)-propenoic acid

D: bismuth bis [3-phenylsulfonyl-2(E)-propenoate] chloride hexahydrate

E: (S)-arginine salt of 3-phenylsulfonyl-2(E)-propenoic acid

F: (S)-lysine salt of 3-phenylsulfonyl-2(E)-propenoic acid

G: bismuth tris [3-phenylthio-2(E)-propenoate] trihydrate

H: zinc bis [3-phenylsulfonyl-2(E)-propenoate] tetrahydrate.

The compounds of the invention were tested for their biological activity by the following methods.

(1) Assay of gastric injuries induced by acidic alcohol [A. Robert, Gastroenterology, 77, 761–767 (1979)]

Female rats weighing about 120 to 150 g fasted for 24 hours were used in this test. Test compounds suspended with Tween 80 were given orally to the animals through an intragastric tube. After a certain period (pretreatment time) acidic alcohol was given through the intragastric tube at a dose or 0.5 ml per 100 g of body weight. The animals were sacrificed after 1 hour, their stomach was removed and incised along the great curve. The length of the reddish-brown strips (haemorrhagic lesions) was measured and the mean total length per stomach was calculated. The biological activity of the test compounds was given compared to the control group. The results are shown in Tables 1 and 2 below.

TABLE 1

| Compound | $ED_{50}$ p.o. (pretreatment: 30 min) |
|---|---|
| A | 4.0 mg/kg |
| C | 3.6 mg/kg |
| D | 3.1 mg/kg |
| F | 4.1 mg/kg |
| H | 3.2 mg/kg |
| Reference compound: Sucralfat | 150 mg/kg |

TABLE 2

| Compound | % Inhibition at a dose of 10 mg/kg p.o. (pretreatment: 30 min) |
|---|---|
| B | 61 |
| E | 73 |

(2) Assay of the inhibition of gastric acid secretion by using pylorus ligature [Shay et al., Gastroenterology, 5, 43–61 (1945)]

Before ligating the pylorus the test compounds suspended with Tween were given orally at a volume of 0.5 ml per 100 mg of body weight to female Wistar rats fasted previously for 20 hours. The animals were sacrificed 4 hours after the operation, and the amount of the acid in the stomach was measured by titration with 0.01N sodium hydroxide solution in the presence of phenolphtalein indicator. The pH value of the content of the stomach was measured by using a pH-meter (Radelkis, Type OP-211/1). The results are shown in Table 3.

TABLE 3

| Compound | $ED_{50}$ p.o. (pretreatment: 30 min) |
|---|---|
| A | 8.6 mg/kg |
| C | 11.0 mg/kg |
| D | 12.0 mg/kg |
| H | 8.0 mg/kg |

TABLE 4

| Compound | % Inhibition in the amount of the acid at a dose of 25 mg/kg p.o. (pretreatment: 30 min) |
|---|---|
| E | 56 |
| F | 50 |
| G | 15 |

Therapeutic significance of the compounds according to the invention is further increased by the fact that they have bactericidal activity against Campylobacter pylori, the presence of which is a risk factor in the emergence of ulcers, or the healing of an ulcer of the digestive tract is influenced negatively by the presence of this bacterium [Internist, 29, 745–754,(1988)].

The activity of the compounds of the present invention against Campylobacter pylori was investigated by agar diffusion and agar dilution assays. The experiments were carried out with Campylobacter pylori cultures isolated from 5 different ulcerous patients. The MIC (minimal inhibitory concentration) value of compound D was found to be from 250 to 1000 μg/ml.

Toxicological data of the compounds of the invention are also beneficial. No death was observed when the compounds of the invention were given orally at a single dose of 1000 mg/kg of body weight.

According to a second aspect of the present invention, novel acrylic acid salts of formula

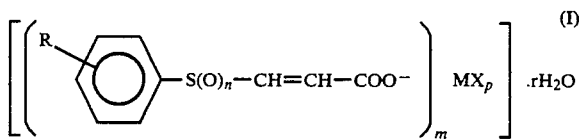

wherein

R represents a hydrogen or a halogen atom, a $C_{1-4}$alkyl, a $C_{1-4}$alkoxy or a nitro group, M represents a cation derived from bismuth, zinc or a pharmaceutically acceptable organic base, X represents an inorganic anion, n is an integer of from 0 to 2, m is an integer of from 1 to 3, p is 0 or 1, and r is an integer of from 0 to 6 may be prepared by any suitable process, for example by reacting a compound of formula

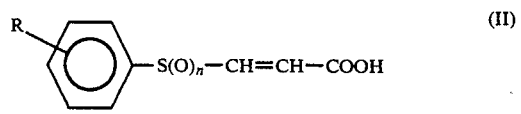

wherein R is as defined hereinbefore, or a salt of this compound formed with an alkali metal hydroxide with a bismuth or zinc salt of an inorganic acid; or with a pharmaceutically acceptable organic base or a hydrohalide salt thereof.

Compounds of formula (I) may be in (E) or (Z) configuration. Further, they may be isolated in anhydrous form or may be crystallized as mono- or oligohydrates.

Compounds of formula (I) of the present invention may be prepared either directly from an acrylic acid derivative of formula (II), or a compound of formula (II) may be converted to a water soluble salt form, preferably to a sodium salt which is further converted to the desired salt of the invention.

Bismuth and zinc salts of the present invention may be prepared in an aqueous alcoholic medium from an alkali metal salt of a compound of formula (II), which in turn, is prepared in situ from a compound of formula (II) and a stoichiometric amount of an alkali metal hydroxide, preferably a solution of sodium hydroxide.

Salts of formula (I) formed with organic bases e.g. monoethanolamine or proteinogenic amino acids may be prepared directly from the starting compounds of formula (II) by salification in an inert organic solvent, preferably methanol or ethanol.

Bismuth and zinc salts of formula (I) may be prepared from different salts preferably chloride, sulfate or nitrate salts of bismuth and zinc, respectively.

For the preparation of a compound of formula (I), wherein p is zero, the salification reaction is carried out at slightly elevated temperatures, preferably about 40° C.

Salification with an organic base is carried out with stoichiometric amount of a base at room temperature, in an alcohol-type solvent for about 1 to 2 hours, then the solvent is evaporated and the salt is crystallised from a poor solvent, preferably acetonitrile, diethyl ether etc.

Bismuth and zinc salts of formula (I) can be dissolved in water very poorly; therefore no organic solvent is needed to precipitate them. These salts may be precipitated in a hydrate form depending on the reaction conditions.

Starting materials may be prepared according to known methods described e.g. by H. Hogeveen [Recueil, 83, 813 (1964)].

According to a third aspect of the present invention, there are provided pharmaceutical compositions comprising, as active ingredient at least one compound of formula (I) and/or a pharmaceutically acceptable salt thereof with at least one pharmaceutical carrier or excipient, for parenteral or enteral administration. These pharmaceutical compositions may be used in the prophylaxis or treatment of ulcerations. The carrier or excipient must be nontoxic and pharmaceutically acceptable by the recipient, and may be a solid or liquid one. Suitable carriers are e.g. water, gelatin, lactose, strach, pectin, magnesium stearate, stearic acid, talc, vegetable oils such as peanut oil, olive oil, etc. The active ingredient may be formulated in a conventional manner e.g. to a solid composition such as tablet, lozenge, dragee, capsule, like gelatin capsule, pill, etc.

Pharmaceutical compositions of the invention optionally may contain one or more conventional excipients e.g. preservatives, stabilizing agents, wetting agents, emulgeators, etc. and further active ingredients exerting no synergistic activity in the given combination.

These formulations may be prepared by any suitable method, e.g. in the case of solid formulations by sieving, admixing, granulating and compressing the ingredients. The so-obtained formulations may be subjected to conventional after-treatments well known in pharmaceutical technology, e.g. sterilization. The amount of the active ingredient may be varied within a wide range, e.g. about from 0.01 to 95% by weight in these formulations.

A preferable tablet formulation of the invention may contain in addition to the active ingredient a filler, e.g. microcrystalline cellulose and/or polyvinylpyrrolidone, a disintegrator, e.g. starch and/or carboxymethyl starch, as well as an antiadhesion agent or lubricant, e.g. magnesium stearate and/or talc.

A preferable capsule formulation according to the present invention may include an above mentioned inert filler, disintegrator and/or lubricant.

A preferable suspension formulation of the present invention can be prepared by evenly dispersing the finely divided active ingredient in a syrup containing a flavoring agent, e.g. raspberry or strawberry aroma; a coloring agent; a food dye; a viscosity increasing agent e.g. Carbopole; a wetting agent, e.g. Tween, as well as a preservative e.g. sodium benzoate.

According to a fourth aspect of the present invention, there is provided a method of treating or preventing ulceration in mammals inclusive of man by using a compound of formula (I) wherein R is a defined hereinbefore or a pharmaceutical composition containing such a compound in an amount sufficient to ensure the desired healing or preventing effect.

According to a fifth aspect of the present invention, there is provided the use of a compound of formula (I) wherein R is a defined hereinbefore in the preparation of a pharmaceutical composition for the prophylaxis or treatment of ulceration in mammals, inclusive of man.

The dosage regimen of the active ingredient may be varied within a wide range depending on various factors such as the nature of the active ingredient in question, the species, age and body weight of the subject to be treated, the severity and symptoms of the disease, etc., therefore the exact dose must be prescribed by the physician individually in each case. In general, the dosage may vary about from 10 to 200 mg active ingredient per day per adult in the case of enteral administration.

For a better understanding of the invention, the following non-limiting Formulation Examples and Working Examples are given to illustrate the preparation of pharmaceutical compositions and the compounds of formula (I), respectively.

EXAMPLE I

Tablet formulation

The active ingredient was measured, sieved and homogenized with the fillers then admixed with the microcrystalline cellulose. The whole mixture was granulated with an aqueous solution of polyvinylpyrrolidone, then dried. The granulate first was mixed with the disintegrator then the whole mixture was homogenized with the antiadhesion agents and lubricants. The homogenous granules were compressed into tablets.

| Composition of tablets | | |
|---|---|---|
| | Active ingredient | |
| Amount | D | H |
| active ingredient | 10.0 mg | 20.0 mg |
| colloidal hydrophilic silica | 0.7 mg | 1.5 mg |
| magnesium stearate | 1.5 mg | 3.0 mg |
| polyvinylpyrrolidone | 3.0 mg | 6.0 mg |
| talc | 4.5 mg | 9.0 mg |
| sodium carboxymethylamylopect. | 6.0 mg | 12.0 mg |
| mycrocrystalline cellulose | 6.3 mg | 18.5 mg |
| corn starch | 40.0 mg | 80.0 mg |
| lactose | 78.0 mg | 150.0 mg |
| total weight | 150.0 mg | 300.0 mg |

EXAMPLE II

Suspension formulation

Sugar and sterile water were cooked to give a syrup. Carbopole was swelled in sterile water then mixed with the syrup. The finely divided active ingredient was intimately admixed with the surface active agents then dispersed with the viscous syrup. The coloring and flavoring agent and preservative were dissolved in sterile water then admixed to the suspension. The suspension was homogenized, filled into ampoules or plastic containers while ensuring the homogenity of the mixture.

| Amount | Composition of suspension Active ingredient D | H |
| --- | --- | --- |
| active ingredient | 1.00 g | 1.00 g |
| raspberry aroma | 1.00 g | 0.40 g |
| FD + C red No 40 | 0.03 g | 0.01 g |
| citric acid | 0.97 g | 0.33 g |
| sodium benzoate | 0.90 g | 0.30 g |
| polyacrylic acid | 1.20 g | 0.40 g |
| sorboxaethen olienicum | 0.10 g | 0.03 g |
| sucrose | 150.00 g | 50.00 g |
| distilled water | ad 300.00 g | ad 150.0 g |
| Suitable administration | 50 mg/spoonful | 50 mg/teaspoonful |

EXAMPLE 1

Bismuth tris[3-phenylsulfonyl-2(E)-propenoate] pentahydrate

3-Phenylsulfonyl-2(E)-propenoic acid (3.18 g, 15 mmol) in ethanol (100 ml) was salified with a 3% aqueous solution of sodium hydroxide (20 ml) then the whole mixture was added dropwise to a solution of bismuth trichloride (1.57 g, 5 mmol) in ethanol (250 ml) at 40° C. After stirring for 3 hours, the precipitated solid was filtered off, washed with water and dried to give the desired product (3.35 g, 72%).

Melting point: 235° to 240° C. (with decomposition).

Molecular formula: $C_{27}H_{21}BiO_{12}S_3 \cdot 5H_2O$ (Mw: 932.68) according to the elementary analysis data.

Bi content according to complexometric titration:
calculated: 22.40%
found: 22.60%.

EXAMPLE 2

Zinc bis[3-phenylthio-2(Z)-propenoate] hydrate

3-Phenylthio-2(Z)-propenoic acid (7.2 g, 40 mmol) was dissolved in a 5% solution of sodium hydroxide (32 ml), and the solution was added to a solution of zinc sulfate heptahydrate (5.75 g, 20 mmol) in water (40 ml). A spontaneous precipitation was observed. After stirring for 10 minutes, the solid was filtered off and washed with water to give the desired product (7.9 g, 89%). Melting point: 180° C. (with decomposition)

Molecular formula: $C_{18}H_{14}O_4S_2Zn \cdot H_2O$ (Mw: 441.82) according to the elementary analysis data.

Zn content according to complexometric titration:
calculated: 14.79%
found: 14.77%.

EXAMPLE 3

Monoethanolamine salt of 3-phenylsulfonyl-2(E)-propenoic acid

A solution of monolthanolamine (0.61 g, 10 mmol) in methanol (5 ml) was added to a solution of 3-phenylsulfonyl-2(E)-propenoic acid (2.12 g, 10 mmol) in methanol (20 ml). After stirring for 1 hour, the solvent was evaporated and the residual solid was suspended in diethyl ether, then filtered off to give the desired product (2.54 g, 93%).

Melting point: 184° C. (with decomposition).

EXAMPLE 4

Bismuth bis[3-phenylsulfonyl-2(E)-propenoate] chloride hexahydrate

A solution of sodium hydroxide (2.4 g, 60 mmol) in water (50 ml) was added to a solution of 3-phenylsulfonyl-2(E)-propenoic acid (12.72 g, 60 mmol) in ethanol (150 ml), then the whole mixture was added to a solution of bismuth trichloride (6.3 g, 20 mmol) in ethanol (600 ml). After stirring for 2 hours, the precipitate was filtered off, washed with water and ethanol, then dried to give the desired product (14.9 g, 96%).

Melting point: 244° C. (with decomposition).

Molecular formula: $C_{18}H_{14}BiClO_8S_2 \cdot 6H_2O$ (Mw: 774.93) according to the elementary analysis data.

Bi content according to complexometric titration:
calculated: 27.0%
found: 27.1%.

EXAMPLE 5

(S)-Arginine salt of 3-phenylsulfonyl-2(E)-propenoic acid

A solution of 3-phenylsulfonyl-2(E)-propenoic acid (2.12 g, 10 mmol) in methanol (15 ml) was added to a solution of (S)-arginine (1.74 g, 10 mmol) in water (15 ml). After stirring for 1 hour, the solvent was evaporated and the residue was suspended in acetonitrile (200 ml), filtered off and washed with acetonitrile to give the desired product (3.55 g, 92%).

Melting point: 184° to 185° C. (with decomposition).

Molecular formula: $C_{15}H_{22}N_4O_6S$ (Mw: 386.42) according to the elementary analysis data.

$[\alpha]_D^{25}: +3.99°$ (c=1, water).

EXAMPLE 6

(S)-Lysine salt of 3-phenylsulfonyl-2(E)-propenoic acid

A solution of 3-phenylsulfonyl-2(E)-propenoic acid (2.12 g, 10 mmol) in methanol (25 ml) was added to a solution of (S)-lysine (1.46 g, 10 mmol) in methanol (50 ml). After stirring for 4 hours, the precipitated salt was filtered off and washed with diethyl ether to give the desired product (2.96 g, 83%).

Melting point: 190° to 191° C. (with decomposition).

$[\alpha]_D^{25}: +3.97$ (c=1, water).

EXAMPLE 7

Bismuth tris[3-phenylthio-2(E)-propenoate] trihydrate

A solution of sodium hydroxide (0.72 g, 18 mmol) in water (5 ml) was added to a solution of 3-phenylthio-2(E)-propenoic acid (3.24 g, 18 mmol) in ethanol (50 ml), then the whole mixture was added to a solution of bismuth trichloride (2.07 g, 6.6 mmol) in ethanol (200 ml). After stirring for 2 hours, ethanol was evaporated and the residue was triturated with water, filtered off and washed with water to give the desired product (4.0 g, 83%).

Melting point: 197° to 228° C. (with decomposition).

Molecular formula: $C_{27}H_{21}BiO_6S_3 \cdot 3H_2O$ (Mw: 800.66) according to the elementary analysis data.

Bi content according to complexometric titration:
calculated: 26.1%,
found: 26.6%.

EXAMPLE 8

(S)-Lysine salt of 3-(4-chlorophenylsulfony)-2(E)-propenoic acid

A 33% solution of hydrogen peroxide (25.4 g, 0.2 mol) was added to a solution of 3-(4-chlorophenylthio)-2(E)-propenoic acid (21.5 g, 0.1 mol) in glacial acetic acid (150 ml). After stirring the solution for 2 hours at 90° to 100° C., the solvent was evaporated and the solid residue was recrystallised from glacial acetic acid to give 3-(4-chlorophenylsulfonyl)-2(E)-propenoic acid (21 g, 85%).

The so-obtained 3-(4-chlorophenylsulfonyl)-2(E)-propenoic acid was dissolved in methanol (30 ml) and a solution of (S)-lysine (1.46 g, 10 mmol) in methanol (50 ml) was added to it. After stirring for 2 hours, the precipitated salt was filtered off and washed with methanol to give the desired product (2.88 g, 74%).

Melting point: 204° to 205° C. (with decomposition). $[\alpha]_D^{25}$: +3.91 (c=1, water).

EXAMPLE 9

Zinc bis[3-phenylsulfonyl-2(E)-propenoate] tetrahydrate

A mixture of 3-phenylsulfonyl-2(E)-propenoic acid (4.24 g, 20 mmol) and zinc oxide (0.82 g, 10 mmol) in water (30 ml) was stirred at 100° C. for 2 hours, then at 5° C. for an additional 2 hours. The precipitated solid was filtered off, washed with ice water and ethanol, then dried to give the desired product (3.45 g, 71%).

Melting point: initial melting at 85° C., then decomposition at 102° C.

Molecular formula: $C_{18}H_{14}O_8S_2Zn \cdot 4H_2O$ (Mw: 487.8) according to the elementary analysis data.

Zn content:
calculated: 11.67%
found: 12.87%.
Water content:
calculated: 11.76%
found: 12.58%.

We claim:

1. A compound of formula

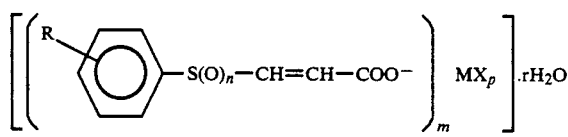

wherein
R represents a hydrogen or a halogen atom, a $C_{1-4}$alkyl, a $C_{1-4}$alkoxy or a nitro group,
M represents a cation derived from bismuth, zinc or a pharmaceutically acceptable organic base,
X represents an inorganic anion,
n is an integer of from 0 to 2,
m is an integer of from 1 to 3,
p is 0 or 1, and
r is an integer of from 0 to 6.

2. A process for the preparation of a compound of formula

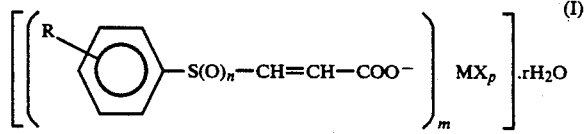

wherein
R represents a hydrogen or a halogen atom, a $C_{1-4}$alkyl, a $C_{1-4}$alkoxy or a nitro group,
M represents a cation derived from bismuth, zinc or a pharmaceutically acceptable organic base,
X represents an inorganic anion,
n is an integer of from 0 to 2,
m is an integer of from 1 to 3,
p is 0 or 1, and
r is an integer of from 0 to 6 which comprises reacting a compound of formula

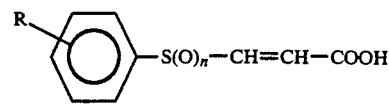

wherein R is as hereinbefore defined, or an alkali metal salt thereof with a bismuth or zinc salt of an inorganic acid, or with a pharmaceutically acceptable organic base or a hydrohalide salt thereof.

3. A process according to claim 2, wherein the pharmaceutically acceptable organic base is monoethanolamine, arginine or lysine.

4. A process according to claim 3, wherein the inorganic anion X is a halide anion.

5. A process according to claim 2, wherein the bismuth or zinc salt formed with an inorganic acid is bismuth or zinc halide, preferably chloride.

6. A pharmaceutical composition for treating an ulcer comprising, as active ingredient a therapeutically effective amount of a compound of the formula

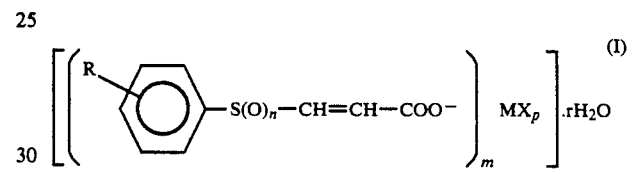

wherein
R represents a hydrogen or a halogen atom, a $C_{1-4}$-alkyl, a $C_{1-4}$alkoxy or a nitro group,
M represents a cation derived from bismuth, zinc or a pharmaceutically acceptable organic base,
X represents an inorganic anion,
n is an integer of from 0 to 2,
m is an integer of from 1 to 3,
p is 0 or 1, and
r is an integer of from 0 to 6
together with a pharmaceutically acceptable inert carrier.

7. A method for treating or preventing ulceration in the digestive tract of a mammal, which comprises using a therapeutically effective amount of compound of formula

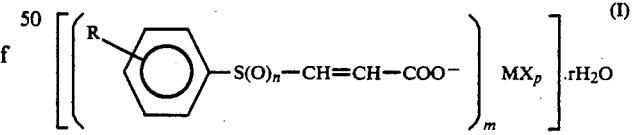

wherein
R represents a hydrogen or a halogen atom, a $C_{1-4}$-alkyl, a $C_{1-4}$alkoxy or a nitro group,
M represents a cation derived from bismuth, zinc or a pharmaceutically acceptable organic base,
X represents an inorganic anion,
n is an integer of from 0 to 2,
m is an integer of from 1 to 3,
p is 0 or 1, and
r is an integer of from 0 to 6
or a pharmaceutical composition containing such a compound in an amount sufficient to ensure the desired healing or preventing effect.

8. The compound of the Formula (I) defined in claim 1 which is bismuth tris {3-phenylsulfonyl-2(E)-propenoate} pentahydrate.

9. The compound of the Formula (I) defined in claim 1 which is zinc bis{phenylthio-2(Z)-propenoate} hydrate.

10. The compound of the Formula (I) defined in claim 1 which is 3-phenylsulfonyl-2(E)-propenoic acid in the form of the monoethanolamine salt.

11. The compound of the Formula (I) defined in claim 1 which is bismuth bis{3-phenylsulfonyl-2(E)-propenoate} chloride hexahydrate.

12. The compound of the Formula (I) defined in claim 1 which is 3-phenylsulfonyl-2(E)-propenoic acid in the form of the (S)-arginine salt.

13. The compound of the Formula (I) defined in claim 1 which is 3-phenylsulfonyl-2(E)-propenoic acid in the form of the (S)-lysine salt.

14. The compound of the Formula (I) defined in claim 1 which is zinc bis{3-phenylsulfonyl-2(E)-propenoate} tetrahydrate.

* * * * *